(12) United States Patent
Berwe et al.

(10) Patent No.: US 6,365,784 B1
(45) Date of Patent: Apr. 2, 2002

(54) PREPARATION OF ETHYLENE BY GAS PERMEATION

(75) Inventors: Hermann Berwe, Nörvenich-Pingsheim; Rüdiger Knauf, Aull; Herbert Neumann, Bergheim; Matthias Stumpf, Wiesbaden; Manfred Wolter, Erftstadt, all of (DE)

(73) Assignee: Axiva GmbH (DE)

( * ) Notice: Subject to any disclaimer, the term of this patent is extended or adjusted under 35 U.S.C. 154(b) by 0 days.

(21) Appl. No.: 09/529,520

(22) PCT Filed: Oct. 10, 1998

(86) PCT No.: PCT/EP98/06430

§ 371 Date: Jul. 27, 2000

§ 102(e) Date: Jul. 27, 2000

(87) PCT Pub. No.: WO99/20591

PCT Pub. Date: Apr. 29, 1999

(30) Foreign Application Priority Data

Oct. 16, 1997 (DE) .......................................... 197 45 806

(51) Int. Cl.[7] .............................................. C07C 45/34

(52) U.S. Cl. .................... 568/475; 568/449; 568/469.9; 568/470

(58) Field of Search .............................. 568/449, 469.9, 568/470, 475

(56) References Cited

U.S. PATENT DOCUMENTS 4,237,073 A * 12/1980 Steppich et al. ............ 568/401
5,062,866 A * 11/1991 Ho ................................ 55/16

FOREIGN PATENT DOCUMENTS

EP     0 006 523     1/1980
EP     0 315 981     5/1989

* cited by examiner

*Primary Examiner*—Sreeni Padmanabhan
(74) *Attorney, Agent, or Firm*—Connolly Bove Lodge & Hutz LLP

(57) ABSTRACT

The invention relates to a process for preparing carbonyl compounds from olefins and an oxidizing agent in which the olefin is oxidized in a reactor, a reaction gas mixture which comprises unoxidized olefin being formed, which comprises separating off unoxidized olefin at least in part from the reaction gas mixture by a membrane process.

15 Claims, 6 Drawing Sheets

PREPARATION OF ETHYLENE BY GAS PERMEATION

This Application is a 371 of PCT/EP98/06430 filed Oct. 10, 1999.

The invention relates to a process for preparing carbonyl compounds from olefins and an oxidizing agent in which the olefin is oxidized in a reactor, a reaction gas mixture which comprises unoxidized olefin being formed.

The invention relates in particular to a process for preparing acetaldehyde by the Wacker-Hoechst process (EP 0 006 523 A1, incorporated into the present application by reference) from the raw materials ethylene and oxygen in the presence of an aqueous catalyst solution (copper(11) chloride and palladium chloride).

The raw materials ethylene and oxygen react, on an industrial scale, in a vertically upright reactor which is filled with the catalyst solution. The ethylene is fed to the reaction by a continuously recirculated gas stream (recycle gas). The gas stream leaving the reactor, which gas stream, in addition to the reaction product acetaldehyde, comprises stream, unreacted ethylene, carbon dioxide ($CO_2$), oxygen ($O_2$) and small amounts of minor components (reaction gas mixture), is conducted off from the reaction compartment and treated by a multistage process.

Water and aldehyde are separated off by a 2-stage condensation (water separation and gas cooler) with subsequent scrubbing. The aldehyde-free recycle gas which, in the standard operating state, can comprise 60–80% by volume ethylene, 3–7% by volume oxygen and 8–25% by volume $CO_2$ as main components, is compressed to compensate for the loss of pressure, admixed with fresh ethylene and fed to the reactor.

To keep the concentrations of ethylene and inert constituents such as $CO_2$, nitrogen, argon, methane and ethane constant in the recyle gas, it is expedient to bleed off a certain gas stream constantly from the system. Because of its considerable ethylene content, it is advantageous to make further use of the gas stream as raw material (world market price of ethylene currently approximately 800-DM/metric ton). For this purpose, it is first cooled to reduce the moisture content, then compressed using compressors and after passing through an absorption dryer, is transmitted via a pipeline to a consumer. If this pathway of offgas utilization is impossible, the offgas must be flared off via a high flare.

Alternatively, there are essentially two possibilities for utilization;

a) thermal utilization and
b) treatment by absorption or adsorption, for example of $CO_2$ in sodium hydroxide solution, and recycling the ethylene to the process.

Ethene regeneration integrated into the process in initially to be preferred to thermal utilization of the offgas. $CO_2$ and $O_2$ could in principle be separated off by an absorption process, but this would be highly complex because of the high $CO_2$ and $O_2$ contents and would intervene in the licensed material cycle.

The object underlying the invention therefore was to improve the process mentioned at the outset by a suitable separation process.

It has now surprisingly been found that this object can be achieved by separating off the unoxidized olefin, ethylene in the specific case, from the reaction gas mixture by the membrane separation process of gas permeation.

Whereas gas permeation in the case of separation of $N_2/O_2$, for example, belongs to the prior art, its potential use in the present case is surprising in that the selectivity of commercially available membranes for the component ethylene ($C_2H_4$) is generally classified as insufficient for a quantitative separation with acceptable yields. Ethylene has a great similarity to methane ($CH_4$), which is enriched by gas permeation industrially (e.g. in natural gas or landfill gas) only to 60% by volume methane, because the loss of methane is excessive at higher concentrations.

The invention therefore relates to a process for preparing carbonyl compounds from olefins and an oxidizing agent in which the olefin is oxidized in a reactor, a reaction gas mixture which comprises unoxidized olefin being formed, which comprises separating off unoxidized olefin at least in part from the reaction gas mixture by a membrane process.

The invention therefore likewise relates to a process for separating off a gaseous olefin from a gas mixture comprising more than 8% by volume carbon dioxide or oxygen, which comprises separating off the olefin from the gas mixture by gas permeation.

In a first particular embodiment, the carbonyl compound is acetaldhyde and/or the olefin is ethene and/or the oxidizing agent is oxygen. The unoxidized olefin can here either diffuse through the membrane or be retained by it. Possible membranes are polymer membranes, preferably polyimide membranes. However, suitable membranes are also membranes or inorganic materials, preferably of ceramic or metal, palladium or platinum being particularly preferred. In further particular embodiments, the absolute pressure on the reaction gas mixture side is in the range from 1 to 80 bar abs., preferably in the range from 3 to 40 bar abs., or the absolute pressure on the permeate side is less than or equal to 2 bar abs., preferably less than or equal to 1 bar abs., particularly preferably less than or equal to 200 mbar abs. The membrane process is preferably carried out at temperatures in the range from 0 to 100° C., preferably in the range from 10 to 40° C. The membranes are preferably present in the form of spirally wound modules or hollow fiber modules.

Particular embodiments are given by the features of the subclaims. One or more of these features can also represent, together or each alone, solutions according to the invention of the object and these features can also be combined in any manner.

An exemplary embodiment of the process according to the invention is described in more detail below with reference to the Wacker-Hoechst process mentioned at the outset and to the FIGS. 1 to 8. No restriction of the invention in any manner is intended by this.

BRIEF DESCRIPTION OF THE DRAWINGS

In the figures:

FIG. 1 illustrates gas separation using membranes: a gas steam (feed) is passed to a membrane by a transport device, for example by means of a compressor. Some of the gas permeates through the membrane and is taken off as permeate; the residual part whose composition has changed owing to the selective permeation of gas components, is passed on as concentrate.

Figure 1:
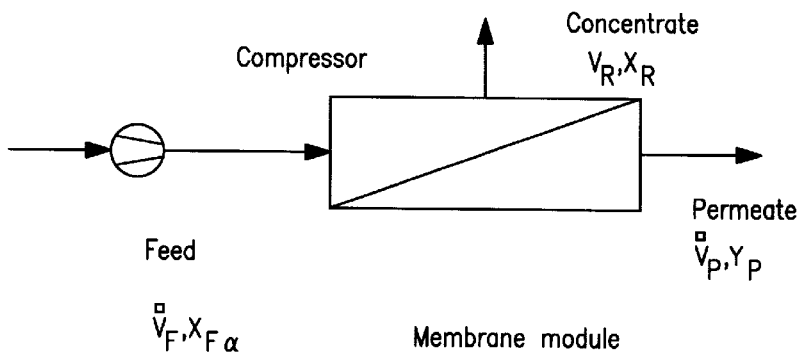
FIG. 1: shows a diagrammatic representation of the principle of gas separation using membranes.
Figure 2:
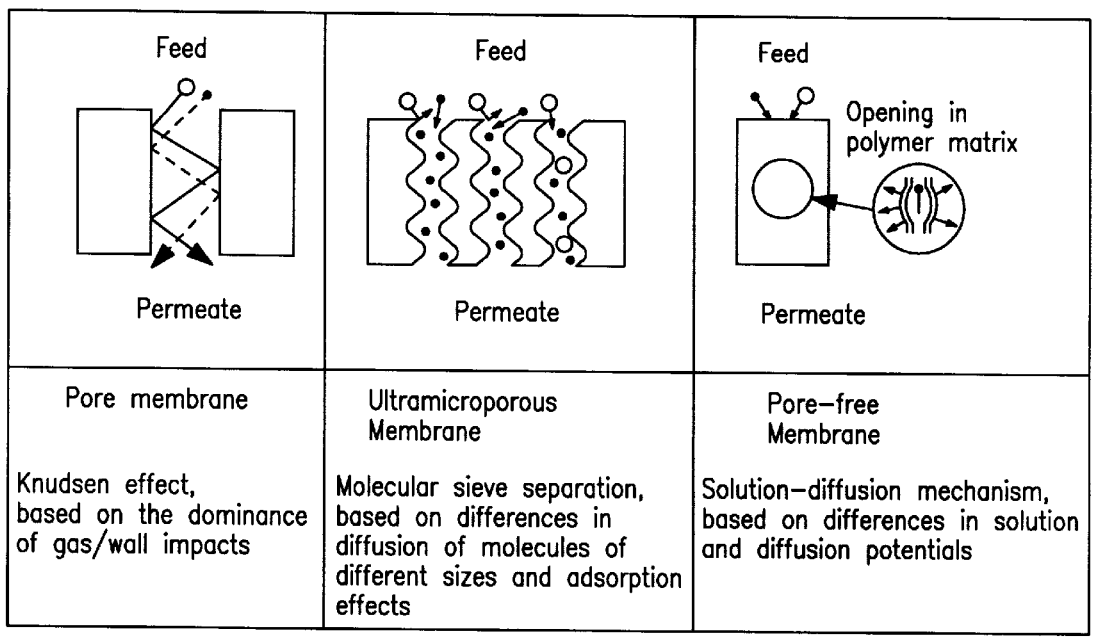
FIG. 2: shows a diagrammatic representation of the separation mechanisms in gas separation using membranes.

As is seen in FIG. 2, a distinction with respect to the separation mechanism is made between gas separation through pore-free, microporous and porous membranes.

Owing to the low selectivity of porous membranes, enrichments are only achievable here by multistage cascades.

With the development of what are termed asymmetric membranes (based on the pore structure, see FIG. 2), whose separating action is based on the solution-diffusion mechanism, the process has also been able to establish itself on an industrial scale for some classes of separation problems.

The separation mechanism (mass transport in membranes) may be derived, as is known, from integrating the generalized formulation of Fick's law for the flux J $$J = -c_{kM} \cdot \frac{D_{kM,0}}{RT} \cdot \frac{\partial \mu_{kM}}{\partial z} \quad (1)$$

over the solution-diffusion layer with the preconditions:
a) no coupling between the permeate fluxes,
b) equality of the chemical potential between the exterior and membrane phase on both sides of the active layer ($\mu_k = \mu_{k,M}$) and the linear relationship $$J = Q_k \cdot (x_k P_F - Y_k P_P) \quad (2),$$

the variables and constants having the customary meanings in this context. Accordingly, the molar flux of each permeating component is proportional to the difference between the partial pressures of this component on both sides of the membrane. The permeability $Q_k$ related to the membrane thickness is a parameter specific to substance and membrane which must be determined by experiment. It is generally proportional to the diffusivity $D_k$ and to the solubility $S_k$ of component k in the membrane and inversely proportional to the membrane thickness $\delta$:

$$Q_k = \frac{D_k \cdot S_k}{\delta}$$

where $$S_k = \frac{c_{kM}}{p_k} \quad (3)$$

It may be concluded from the remarks on mass transport in solution-diffusion membranes that efficient membranes are distinguished by the fact that the product of solubility and diffusivity in the membrane polymer should be as large as possible for one component of a mixture and as small as possible for the other component(s) of the mixture to be separated. Furthermore, the thickness $\delta$ of the solution-diffusion layer should be as small as possible.

For economic use of gas permeation, the fluxes through symmetrical membranes are much too small, even if separation units (modules) having a high packing density are used. The gas permeation has therefore, similarly to reverse osmosis, not been of interest until the moment when it was possible to increase the permeate flux through asymmetric membranes (FIG. 3. variant A) by a factor of 100 with approximately the same selectivity.

Figure 3:
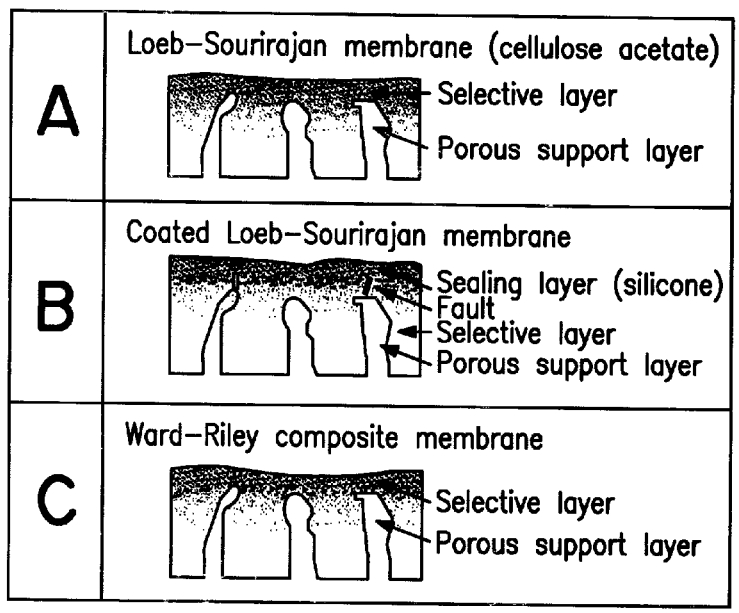
FIG. 3: shows a diagrammatic representation of the structure of gas permeation membranes.

With respect to permeability, the pore-free polymer membranes of each group in FIG. 3 are at least qualitatively similar: thus the membranes in the glass state all have high permeabilities for water vapor, helium, hydrogen and carbon monoxide, but in contrast they are less permeable to nitrogen and methane and ethylene. Solution-diffusion membranes of rubber-like polymers, in contrast, are all distinguished by high permeabilities for organic solvents in comparison with permanent gases such as $O_2$, $N_2$, and are therefore suitable for separating off solvents from exhaust air, for example.

Figure 4:
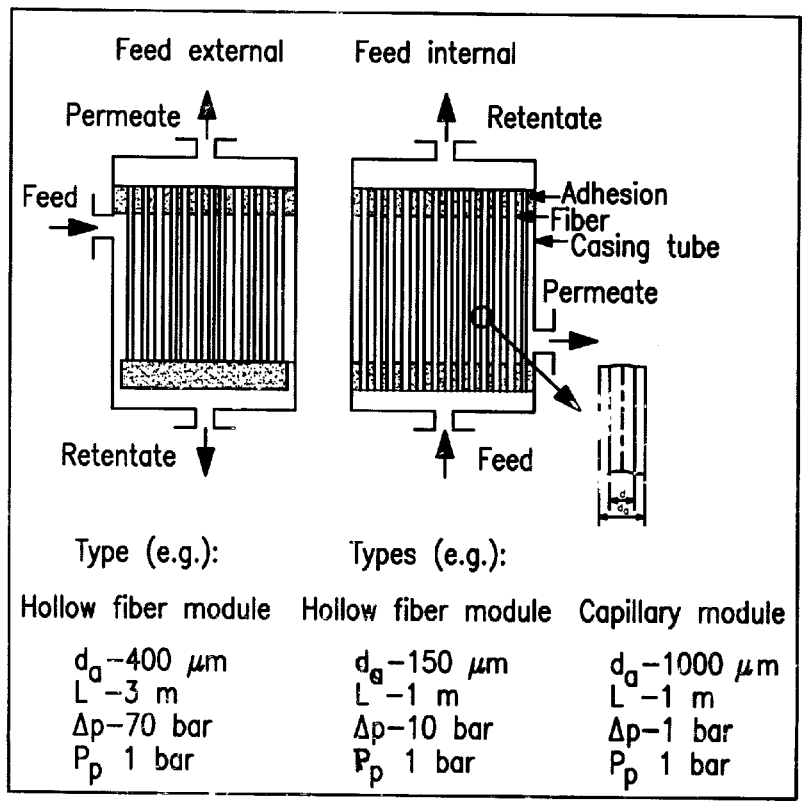
FIG. 4: shows a diagrammatic representation of the structure of hollow fiber modules.

In gas permeation, use is principally made of hollow fiber and capillary modules. In hollow fiber and capillary modules, the membranes are present in the form of very thin pressure-stable tubes. They are either combined in parallel axially or, if they are true hollow fibers, in the shape of a helix, also. In this case, there exist, in accordance with FIG. 4, both modules in which the crude mixture flows on the exterior of the fibers, and modules in which the crude mixture flows in the fibers.

As explained, local mass transport in the separation of mixtures of permanent gases by pore-free polymer membranes can in many cases be described with sufficient accuracy by equation 2. For a binary mixture, the local permeate composition (local separation characteristics) can be calculated in an idealized manner from the local high-pressure side retentate concentration, feed pressure and the permeate pressure, as well as the permeabilities of the membrane. Since binary mixtures are specified by stating one concentration, only the more rapidly permeating component is considered below and the index "i" is omitted (x $\triangleq x_i$, $y \triangleq y_i$). Using equation 2 for both components, on the basis of the mass balance and material balance, after conversion, $$y = \frac{1}{2} \cdot \left[1 + \delta \cdot \left(x + \frac{1}{\alpha - 1}\right)\right] - \quad (3)$$

$$\sqrt{\left[\frac{1}{2} \cdot \left[1 + \delta \cdot \left(x + \frac{1}{\alpha - 1}\right)\right]\right]^2 - \frac{\alpha \cdot \delta \cdot x}{\alpha - 1}} = y(x, \alpha, \delta)$$

Figure 5:
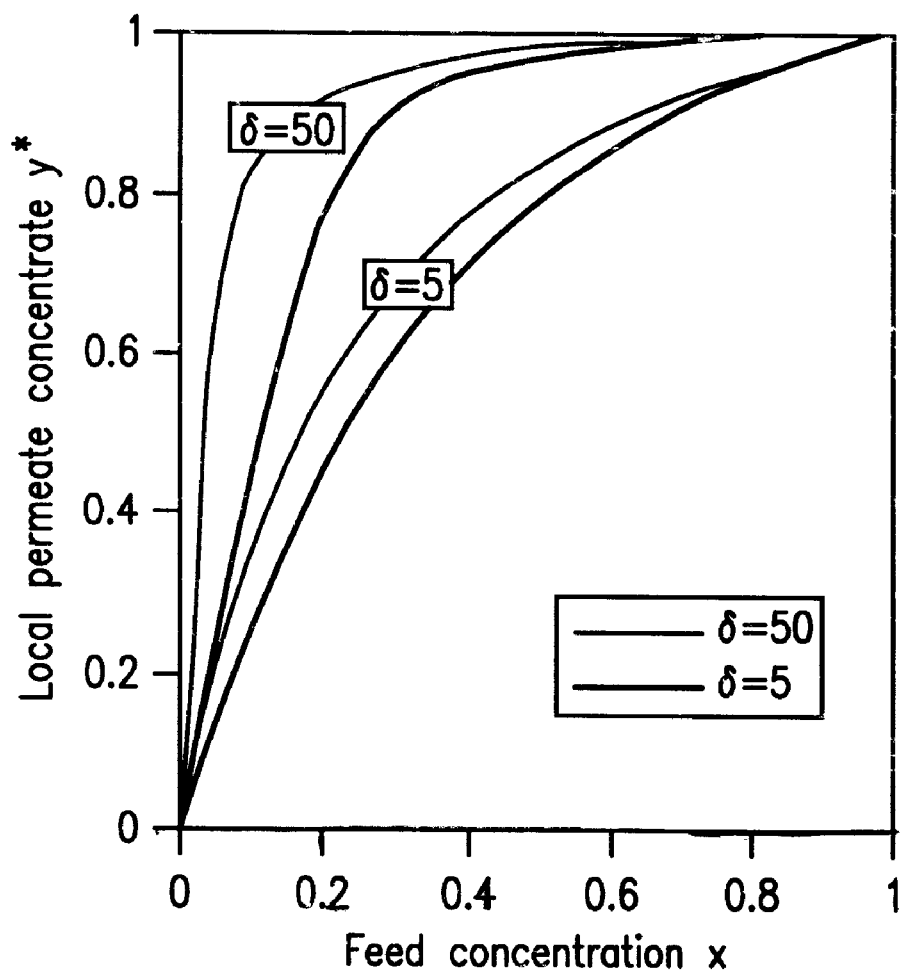
FIG. 5: shows a local separation characteristic.

- ideal separation factor $\alpha = \frac{Q_i}{Q_j} \geq 1$ where pressure ratio $\delta = \frac{p_F}{p_P} \geq 15$ The plot of the equation (3) is shown in FIG. 5.

It can be seen from the diagram that the separation characteristics improve with increasing pressure ratio $\delta$ and with increasing separation factor $\alpha$. Furthermore it is clear that a membrane acts selectively for the more rapidly permeating component over the entire concentration range. This applies even if this component is only present in traces (ppm range), although then the possible accumulation is restricted.

The separation characteristics, in addition to the ideal separation factor $\alpha$, are also restricted by the pressure ratio $\delta$. Unrestricted concentration cannot be achieved even with an ideally selective membrane.

Table 1 shows the mean composition of the ejected ethylene offgas of a large industrial plant over half a year, and the rounded means as base values.

It can be clearly seen that the components ethylene, carbon dioxide, oxygen, argon and nitrogen represent the majority of the gas mixture. The ethylene workup therefore essentially requires separating off $CO_2$ and $O_2$ from the offgas (argon and $N_2$ have lower contents). This separation step can be performed according to the invention by using the membrane process of gas permeation.

TABLE 1

Mean composition of the ethylene offgas

| Component | Mean values | Base values |
|---|---|---|
| Oxygen $O_2$ | 5.84 | 6 |
| Argon Ar | 3 | 3 |
| Nitrogen $N_2$ | 1.03 | 1 |
| Methane $CH_4$ | 0.53 | 0.5 |
| Carbon dioxide $CO_2$ | 11.58 | 12 |
| Ethene $C_2H_4$ | 76.84 | 77 |
| Ethane $C_2H_6$ | 0.69 | 0 |
| Methyl chloride $CH_3Cl$ | 0.62 | 0.5 |
| Vinyl chloride | 0.01 | 0 |
| Acetaldehyde | 0.01 | 0 |
| Ethyl chloride | 0.09 | 0 |
| Furan | 0.04 | 0 |
| Chloroform | 0.0067 | 0 |

Figure 6:
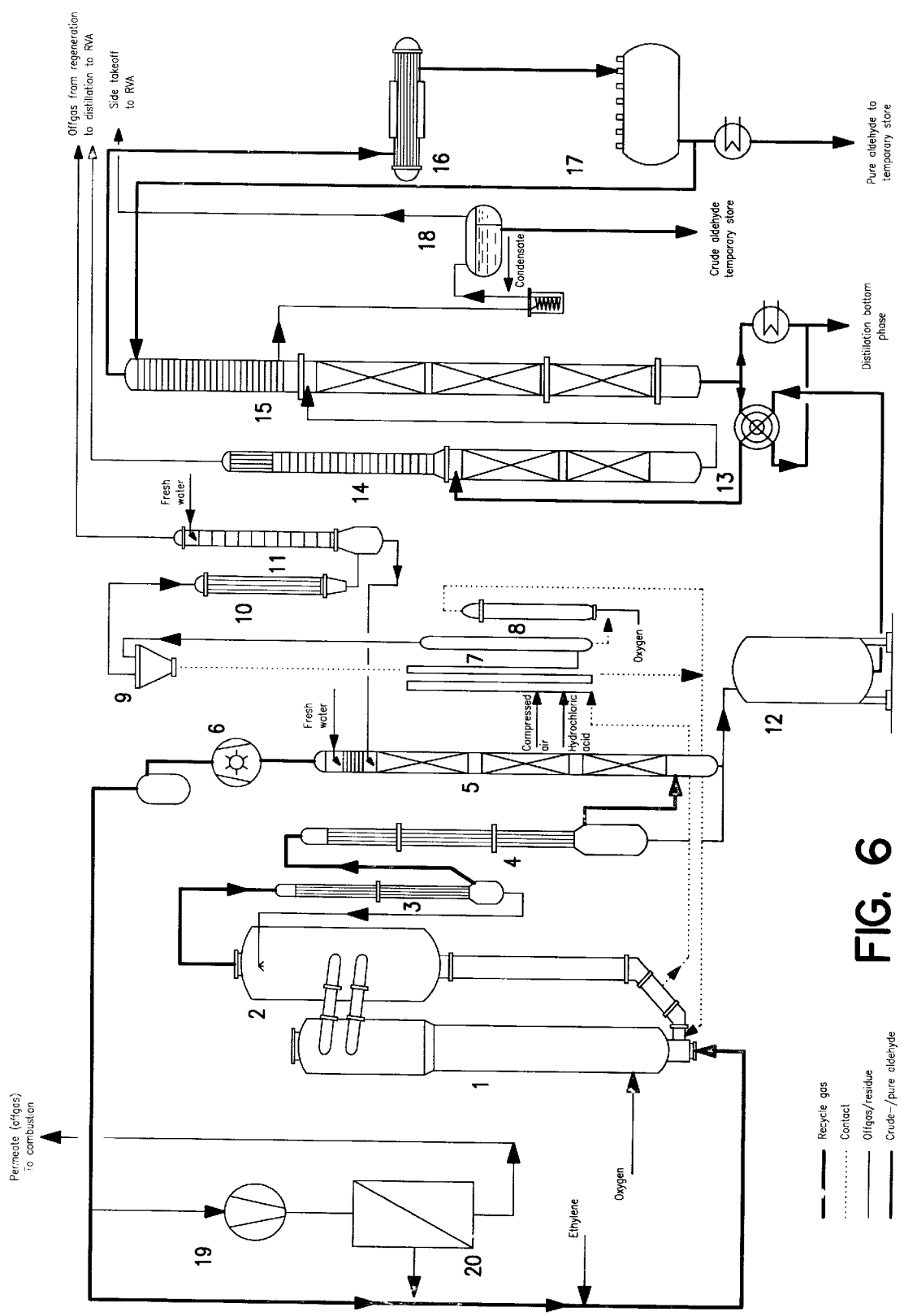
FIG. 6: shows a process flow chart of an exemplary embodiment of the process according to the invention.

FIG. 6 shows the flow diagram of an acetaldehyde production process according to the invention, extended by the gas permeation, the individual reference numbers having the following meanings: 1 reactor, 2 mist eliminator, 3 titanium cooler, 4 gas cooler, 5 gas scrubber, 6 recycle gas fan, 7 contact stripping column, 8 regenerator, 9 vapor separator, 10 vapor cooler, 11 vapor scrubber, 12 crude aldehyde vessel, 13 heat exchanger, 14 degassing column, 15 purification column, 16 condensation, 17 pure aldehyde reservoir, 18 side takeoff separation vessel, 19 piston compressor, 20 membrane unit.

In contrast to the known process, the recyle gas downstream of the gas scrubber is not directly compressed, admixed with fresh ethylene and recirculated to the process, but is first treated according to the invention in a gas permeation unit. Recycle gas compression to high pressures, which is advantageous for gas permeation, can be achieved using compressors.

In addition to the main components, approximately 2% by volume of impurities (byproducts from synthesis) are still present in the recycle gas, which predominantly consist of the components methane, ethane and volatile solvents (e.g. methyl chloride). Although these components do not interfere with respect to concentration of the ethylene to contents >90% by volume, it is advantageous, however, to take into consideration these aspects from below which are relevant to all components:

a) The polymer membranes used in the gas permeation can be sensitive to solvents. Depending on the partial pressure, the temperature and the type of solvents, there is the risk of a change in performance or a restricted service life.

b) Depending on the permeation behavior of all participating components, these can accumulate in the concentrate (ethylene) or in the permeate. In the case of an enrichment on the concentrate side, the effect of the altered recyle gas composition on the reaction should be tested. Advantageous measures for reducing this effect are:

ba) the use of higher purity raw materials (e.g. oxygen) or bb) ejecting enriched components by a side stream, which can be utilized thermally, for example.

Accumulation of by-products in the permeate is advantageous to achieve a separation step having high selectivity. Case must be taken to ensure here that the explosive limits are not exceeded in any stream.

Since the ethylene workup by gas permeation is not prior art, in order to achieve a statement of the suitability and performance (economic efficiency) of a separation process of this type, simulation calculations were carried out in the form of a case study on the basis of existing membrane data and permeabilities.

For these studies on the workup of ethylene offgas by gas permeation, the separation task was specified as follows:

a) volumetric flow rate V of the ethylene offgas to be worked up 700 $m^3/h$ (STP), b) available working pressure of the compressor $p_F$=7 bar (max. 10 bar), c) temperature $\theta$=30° C., d) mean composition of the ethylene offgas in accordance with Table 1 (base values).

e) the purpose of separation is an ethylene content in the concentrate > 90% by volume with an ethylene yield > 70%.

Three membrane types X, Y, Z were compiled from known gas permeabilities (Table 2) and a numerical simulation of the membrane separation process was carried out using these.

TABLE 2

Gas permeabilities used ($m^3/m^2$hbar) for the numerical simulation

| Membrane type Component | X | Y | Z |
|---|---|---|---|
| Ethylene $C_2H_4$ | 0.073 | 0.0135 | 0.015 |
| Carbon dioxide $CO_2$ | 0.43 | 0.351 | 0.3 |
| Oxygen $O_2$ | 0.33 | 0.081 | 0.083 |
| Argon Ar | 0.09 | 0.032 | 0.02* |
| Nitrogen $N_2$ | 0.1 | 0.0162 | 0.01 |
| Methane $CH_4$ | 0.1 | 0.017 | 0.0143 |
| Methyl chloride $CH_3Cl$ | 0.14 | 0.02* | 0.016 |
| Selectivity $CO_2/C_2H_4$ | 5.9 | 26 | 20 |

*estimated

However, an exact process simulation is only possible with difficulty on the basis of these data, since exact data are not available in all cases and the relevant permeabilities of the individual gas components in multicomponent mixtures are greatly dependent on the process conditions (e.g. on the partial pressure).

Figure 7:
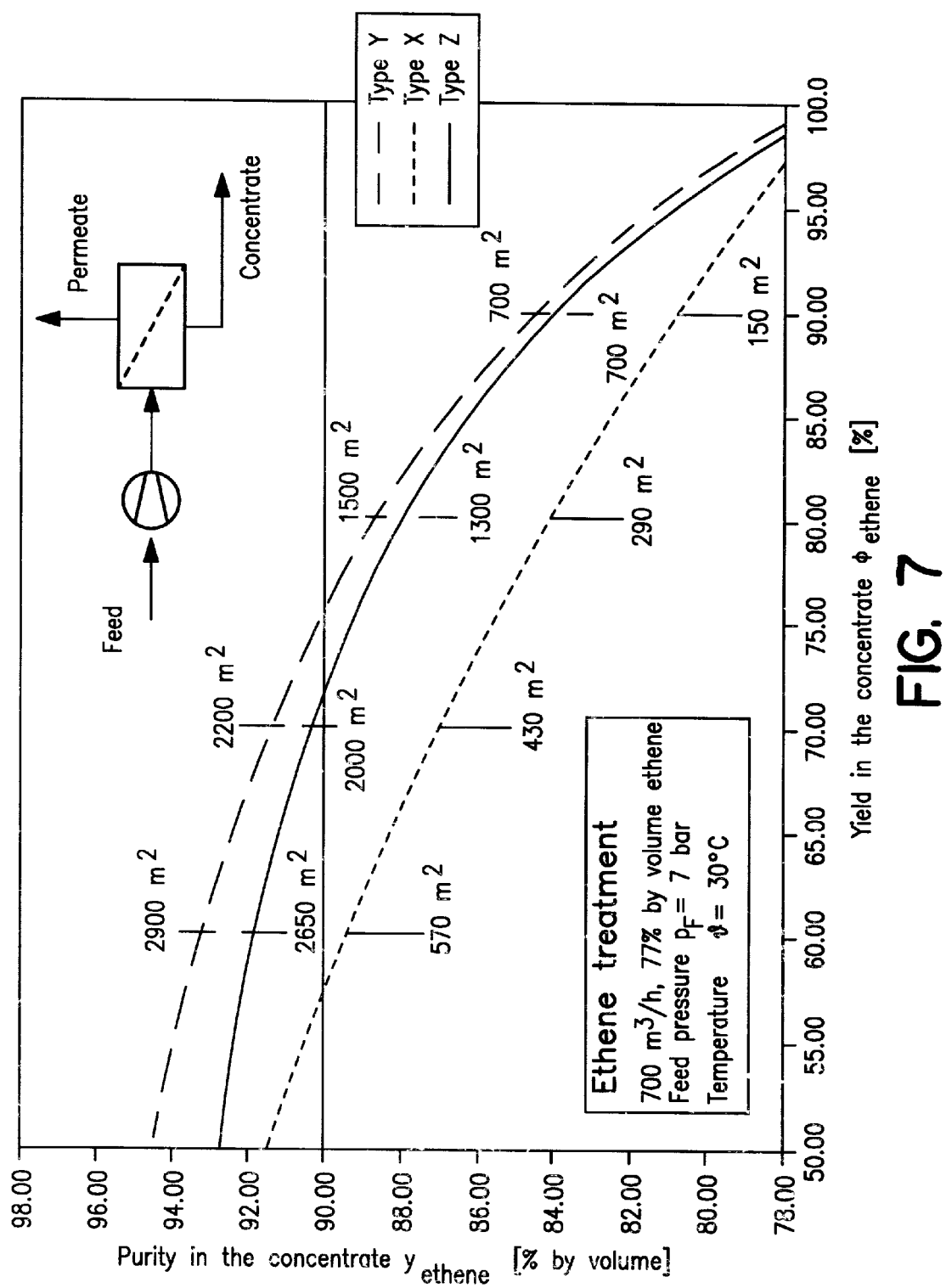
FIG. 7: shows a presentation of the results of a calculation of separation efficiencies for a single-stage membrane separation.

FIG. 7 shows results of the calculations for a single-stage membrane separation. The diagram shows the purity of the ethylene in the concentrate as a function of ethylene yield, i.e. as a function of the respective feed stream content of ethylene to be recovered, for three different membrane types. The graphs result from variation of the membrane surfaces. The membrane separation depletes the feed stream (ethylene offgas) in $CO_2$, as a result of which at the same time the ethylene content increases and the resulting concentrate can be recirculated to the process. The $CO_2$ diffuses through the membrane and passes into the permeate. Since the gas treatment by membranes is based on the relative difference between permeation rates of the participating components, in addition to the desired $CO_2$, ethylene also passes into the permeate.

Depending on the absolute values of the $CO_2$ and ethylene permeabilities, and on their ratio to one another (= ideal membrane selectivity), separations of different efficiency thus result. In general, the membrane surface area to be installed and thus the unit size are approximately inversely proportional to the permeability of a membrane. Furthermore, on account of the finite selectivity of a membrane, with increasing concentration of a material of value (purity of the ethylene in the concentrate), the loss of material of value (decreasing ethylene yield in the concentrate) also increases constantly. The quality of the membrane separation therefore, for the same purity of material of value, increases with increasing yield of material of value. This fact is illustrated for 3 membrane types in FIG. 7.

Figure 8:
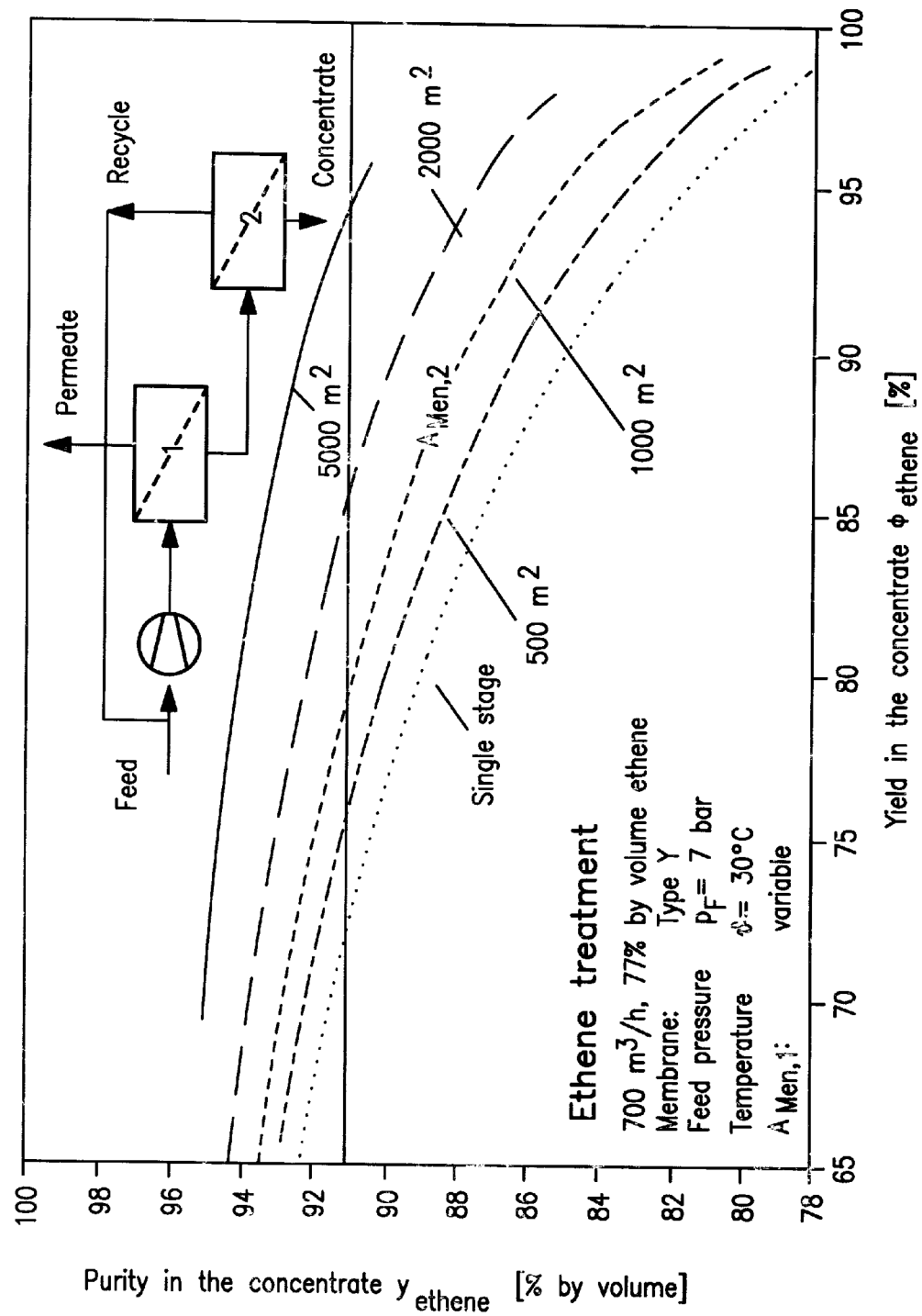
FIG. 8: shows a presentation of the results of a calculation of separation efficiencies for a two-stage membrane separation.

A further increase in ethylene yield can preferably be achieved by multistage units. If the material of value arises on the feed side of the membrane, as is the case with ethylene enrichment, there is the possibility to implement a two-stage membrane separation by simple division of the membrane surface. FIG. 8 shows the results of a two-stage membrane separation in a similar manner to FIG. 7, in which the membrane surface area of the 2nd stage was kept constant at each of a number of different values, while the membrane surface area of the first stage was varied. The ethylene offgas is concentrated in two sequential stages. While the second stage concentrate represents the stream of material of value, the second stage permeate is recirculated to a location upstream of the first stage. In the first stage the ethylene is enriched to a value below the required purity. The permeate produced in this stage has significantly lower ethylene contents owing to the membrane separation characteristics. In contrast, the second stage permeate, which is predominantly formed in the range of high ethylene feed concentrations, has comparatively higher ethylene contents and in consequence contributes to a greater extent to the overall losses of material of value.

FIG. 8 shows that the ethylene yield can be increased by 5–10% in comparison with a single-stage unit.

The studies carried out show that it is possible to work up the ethylene offgas by gas permeation. An ethylene enrichment to >90% by volume can be achieved at a system pressure of 7 bar even in a single stage with an ethylene yield of over 75%. By implementing higher working pressures (to 30 bar, for example, using an additional compressor), the gas permeation unit size can be markedly decreased and the performance (selectivity and thus ethylene yield) can be further increased. An increase in yield is likewise possible by implementing a 2-stage unit circuit with permeate recycling.

The advantages of the process according to the invention are essentially that an economic, process-integrated workup of an offgas stream can be performed using a physical separation process, there is no need for auxiliaries (and thus no interventions into material cycles), and a material of value can be recirculated to the process and thus the process yield can be increased. By implementing the process according to the invention, an equally economical and environmentally friendly increase in efficiency of the overall process can be achieved.

What is claimed is:

1. A process for preparing carbonyl compounds from olefins and an oxidizing agent in which the olefin in a reactor, a reaction gas mixture which comprises unoxidized olefin being formed, which comprises separating off unoxidized olefin at least in part from the reaction gas mixture by a membrane process, and feeding the separated unoxidized ethylene back to the reactor.

2. The process as claimed in claim 1, wherein the carbonyl compound is acetaldehyde.

3. The process as claimed in claim 1, wherein the unoxidized olefin is retained by the membrane.

4. The process as claimed in claim 1, wherein the unoxidized olefin permeates through the membrane.

5. The process as claimed in claim 1, wherein the membrane is a polymer membrane.

6. The process as in claimed in claim 1, wherein the membrane is fabricated from an inorganic material.

7. The process as claimed in claim 3, wherein the absolute pressure on the reaction gas mixture side is in the range from 1 to 80 bar abs.

8. The process as claimed in claim 4, wherein the absolute pressure on the permeate side is less than or equal to 2 bar abs.

9. The process as claimed in claim 5, wherein the membrane process is carried out at temperatures from the range 0 to 100° C.

10. A process as claimed in claim 1, wherein the olefin is ethylene.

11. A process as claimed in claim 1, wherein the oxidizing agent is oxygen.

12. A process as claimed in claim 1, wherein the reaction gas mixture comprises at least 8% by volume carbon dioxide.

13. A process as claimed in claim 5, wherein the membrane is a polyimide.

14. A process as claimed in claim 6, wherein the membrane is palladium.

15. A process as claimed in claim 6, wherein the membrane is platinum.

* * * * *

UNITED STATES PATENT AND TRADEMARK OFFICE
CERTIFICATE OF CORRECTION

| | | |
|---|---|---|
| PATENT NO. | : 6,365,784 B1 | Page 1 of 1 |
| DATED | : April 2, 2002 | |
| INVENTOR(S) | : Hermann Berwe, Rüdiger Knauf, Herbert Neumann, Matthias Stumpf and Manfred Wolter | |

It is certified that error appears in the above-identified patent and that said Letters Patent is hereby corrected as shown below:

Column 8,
Line 8, after "olefin" insert -- is oxidized --

Signed and Sealed this

Eighth Day of October, 2002

Attest:

Attesting Officer

JAMES E. ROGAN
Director of the United States Patent and Trademark Office